United States Patent [19]
Uber et al.

[11] Patent Number: 5,736,739
[45] Date of Patent: *Apr. 7, 1998

[54] RECIRCULATING FILTRATION SYSTEM FOR USE WITH A TRANSPORTABLE ION MOBILITY SPECTROMETER IN GAS CHROMATOGRAPHY APPLICATIONS

[75] Inventors: Robert E. Uber, Allison Park; Viktor Kouznetsov; Alexander Tarassov, both of Mars; Byron L. Carnahan, Pittsburgh; Charles W. Pipich, Monroeville, all of Pa.

[73] Assignee: Mine Safety Appliances Company, Pittsburgh, Pa.

[*] Notice: The term of this patent shall not extend beyond the expiration date of Pat. No. 5,723,861.

[21] Appl. No.: 726,843

[22] Filed: Oct. 8, 1996

Related U.S. Application Data

[63] Continuation-in-part of Ser. No. 628,147, Apr. 4, 1996.

[51] Int. Cl.⁶ .............................. H01J 49/40; H01J 49/04
[52] U.S. Cl. .................................. 250/287; 250/288
[58] Field of Search ........................ 250/287, 288

[56] References Cited

U.S. PATENT DOCUMENTS

| | | |
|---|---|---|
| 4,259,573 | 3/1981 | Proher. |
| 4,317,995 | 3/1982 | Bradshaw. |
| 4,633,083 | 12/1986 | Knorr et al. ............... 250/287 |
| 4,732,046 | 3/1988 | Lawrence ................ 73/864.21 |
| 4,818,264 | 4/1989 | Langhorst ................. 65/4.3 |
| 5,032,721 | 7/1991 | Bacon. |
| 5,218,203 | 6/1993 | Eisele et al. ............... 250/288 |
| 5,420,424 | 5/1995 | Carnahan et al. .......... 250/287 |
| 5,437,179 | 8/1995 | Wiegand et al. ............ 73/23.35 |

FOREIGN PATENT DOCUMENTS 0135747   4/1875   European Pat. Off..

OTHER PUBLICATIONS

Analytical Chemistry –vol. 65, No. 3, 1993, Columbus, US, pp. 299–306, A.P. Snyder, "Portable Hand–Held Gas Chromatography/Ion Mobility Spectrometry Device", See Figure 2.

*Primary Examiner*—Jack I. Berman
*Attorney, Agent, or Firm*—Titus & McConomy

[57] ABSTRACT

Generally, the present invention provides a recirculating filtration system for use with a transportable ion mobility spectrometer in gas chromatography applications. The transportable recirculating filtration system comprises a pump and a set of filters and flow sensors connected to an ion mobility spectrometry sensor having a gas chromatograph column at its inlet. The IMS sensor's outlet flow is cleaned by the filters and recirculated by the pump back into the IMS sensor as the carrier fluid stream flow. A portion of the IMS sensor's outlet flow equal to the amount of flow introduced into the sensor as the sample is exhausted from the filtration system to maintain a constant total flow volume through the system as the sample is being analyzed. Preferably, the multicapillary column is sealed to a heated transfer line leading to the sample stream inlet of the IMS sensor. The transfer line is preferably maintained at a temperature 10° C.–40° C. above that of the multicapillary column in order to ensure that analyte species will not adsorb on the walls of the transfer line instead of entering the sample stream inlet of the IMS sensor. The transfer line can be optionally configured with a flow smoothing insert to produce a laminar flow profile throughout the volume between the transfer line outlet end and the IMS sensor housing upon exit of the carrier flow stream from the flow smoothing insert.

27 Claims, 3 Drawing Sheets

5,736,739

RECIRCULATING FILTRATION SYSTEM FOR USE WITH A TRANSPORTABLE ION MOBILITY SPECTROMETER IN GAS CHROMATOGRAPHY APPLICATIONS

This application is a continuation-in-part of U.S. patent application Ser. No. 08/628,147, filed Apr. 4, 1996.

FIELD OF THE INVENTION

The invention relates generally to a transportable recirculating filtration system for use in conducting measurements with an ion mobility spectrometer, and specifically to a transportable recirculating filtration system for using a field IMS sensor in gas chromatography applications.

BACKGROUND OF THE INVENTION

U.S. Pat. No. 5,420,424 provides a sensor using ion mobility spectrometry (IMS) to detect trace concentration level species present in a sample gas stream. The IMS sensor disclosed in U.S. Pat. No. 5,420,424 utilizes periodic electrical fields to separate different species of ions according to the functional dependence of their mobility with electric field strength. Ions generated in the ionization chamber of the IMS sensor are guided through an ion filter to an ion detector by an electric field known as the "dispersion field." This "dispersion field" is created by an asymmetric periodic radio frequency (RF) voltage applied between a pair of closely spaced longitudinal electrodes. The displacement of the ions induced by the dispersion field is modified or compensated by a second electric field known as the "compensation field." The compensation field is created by an adjustable time independent direct current electrical potential that is applied between the electrodes to isolate a particular ion species for detection as a result of the variance in mobility between particular ion species as a function of electric field strength. This form of ion mobility spectrometry, known as field ion spectrometry (FIS), offers a new method of detecting species present at trace (parts per million to parts per trillion) concentration levels in a sample gas to be analyzed.

To avoid compromising the sensor's performance due to impurities which may be present in the carrier fluid stream that transports the ions through the ion filter, existing IMS sensor designs require connection to a filtration system to clean the carrier fluid stream flow prior to its introduction into the sensor. The use of a stationary filtration source presents a problem if the IMS sensor is to be used as a portable instrument in the detection of atmospheric contaminants in remote locations. Existing portable filtration systems used with IMS devices are not compatible with the IMS design disclosed in U.S. Pat. No. 5,420,424. The present invention solves this problem by providing a recirculating filtration system for use with a transportable IMS sensor of the design disclosed in U.S. Pat. No. 5,420,424 in gas chromatography applications.

Accordingly, the preferred embodiment of the present invention preferably provides a recirculating filtration system for use with a transportable ion mobility spectrometry sensor in gas chromatography applications.

SUMMARY OF THE INVENTION

Generally, the present invention provides a recirculating filtration system for use with a transportable ion mobility spectrometer in gas chromatography applications. One preferred embodiment of the transportable recirculating filtration system comprises a pump connected with a set of filters and flow sensors to an ion mobility spectrometry sensor preferably of the design disclosed in U.S. Pat. No. 5,420,424 through a gas chromatograph column. The IMS sensor's outlet flow is cleaned by the filters and recirculated by the pump back into the IMS sensor. A portion of the IMS sensor's outlet flow equal to the amount of flow introduced into the sample stream inlet of the IMS sensor is exhausted from the filtration system to maintain a constant total flow volume through the system as the sample is being taken.

The gas chromatograph is preferably comprised of a multicapillary column containing a coating comprised of a stationary phase substance. The multicapillary column is in communication with the IMS sensor sample stream inlet for transmitting an unknown concentration level of at least one analyte into the IMS sample stream inlet to be measured by the ion mobility spectrometer. A source of carrier gas in communication with a sample injector entrains the analyte in the sample injector for transport into the multicapillary column. The analyte is soluble in the stationary phase substance such that transport of the analyte into the IMS sample stream inlet is delayed by a predetermined "retention time" interval in the multicapillary column. Variation in the retention time between different analyte species allows the IMS sensor to accurately measure the individual concentrations of the various analyte species since the entry of each analyte species into the IMS sample stream inlet will be staggered as compared to the other species present in the sample stream.

Preferably, the multicapillary column is sealed to a heated transfer line leading to the sample stream inlet of the IMS sensor. The transfer line is preferably maintained at a temperature 10° C.–40° C. above that of the multicapillary column in order to ensure that analyte species will not adsorb on the walls of the transfer line instead of entering the sample stream inlet of the IMS sensor. The transfer line can be optionally configured with a flow smoothing insert to produce a laminar flow profile throughout the volume between the transfer line outlet end and the IMS sensor housing upon exit of the IMS carrier flow stream from the flow smoothing insert.

Other details, objects, and advantages of the present invention will become apparent in the following description of the presently preferred embodiments.

BRIEF DESCRIPTION OF THE DETAILED DRAWINGS

In the accompanying drawings, the preferred embodiments of the present invention and preferred methods of practicing the present invention are illustrated wherein.

DETAILED DESCRIPTION OF THE PREFERRED EMBODIMENT

Figure 1:
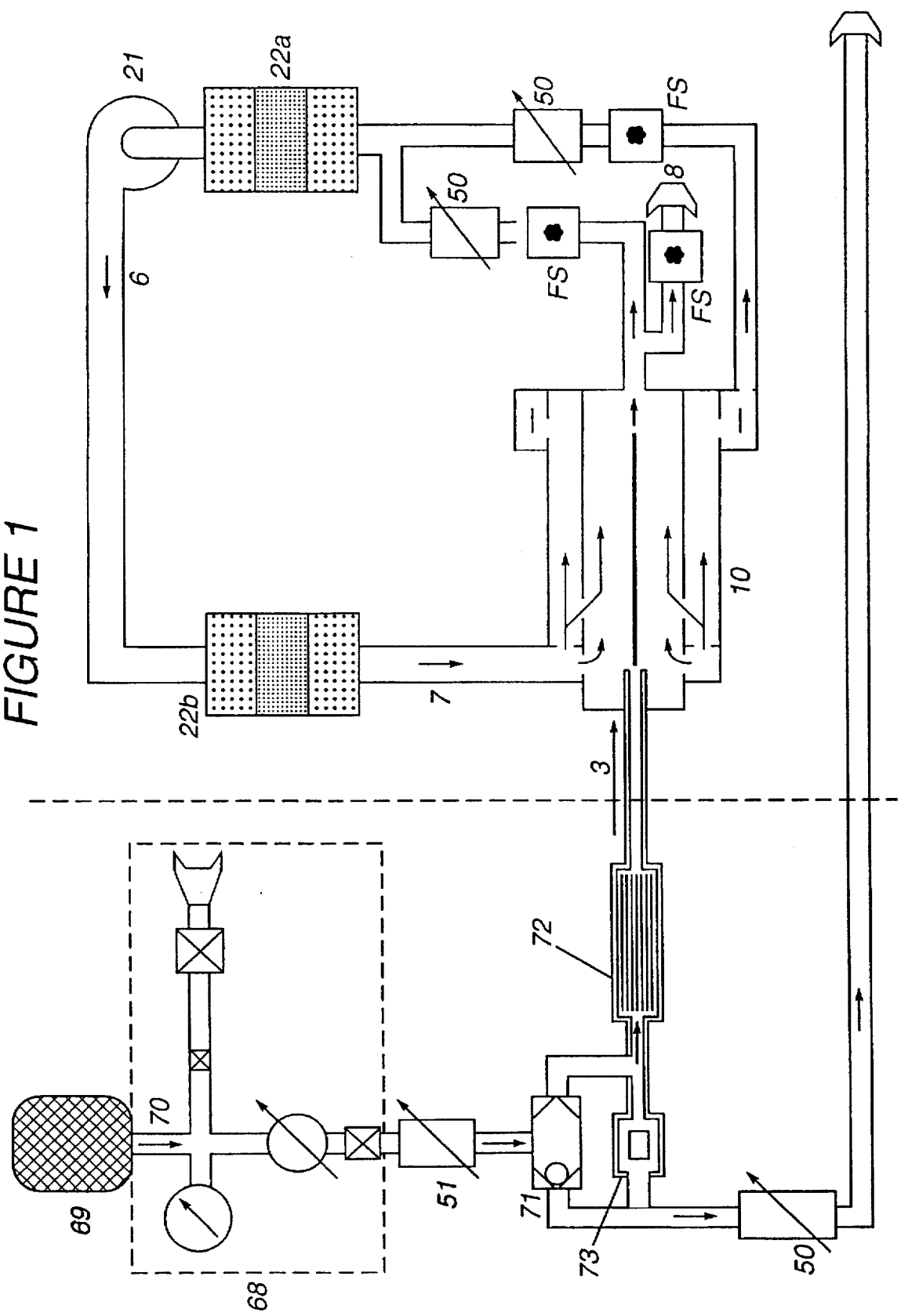
FIG. 1 is a schematic fluid system diagram of a preferred embodiment of the present invention which provides a recirculating filtration system for use with a transportable IMS sensor in gas chromatography applications.

FIG. 1 shows the preferred embodiment of the present invention, which provides a recirculating filtration system using a transportable IMS sensor in gas chromatography applications. The embodiment shown in FIG. 1 comprises a pump 21 in combination with filters 22a and 22b in the inlet and outlet streams thereof, respectively, along with a plurality of flow sensors FS and flow adjustment valves 50 all in communication with an ion mobility spectrometry sensor 10. IMS sensor 10 is preferably of the design described in U.S. Pat. No. 5,420,424, the disclosure of which is incorporated herein by reference. The IMS sensor's outlet fluid flow stream 6 is purified and recirculated back into the IMS sensor 10 as the carrier fluid stream flow 7 described in U.S. Pat. No. 5,420,424. A portion of the outlet fluid flow stream 6 equal to the amount of sample fluid stream flow 3 introduced into the IMS sensor 10 is removed as exhaust 8 from the filtration system, thereby maintaining a constant total flow rate through the system. The flow rates of the sample 3 and exhaust 8 fluid streams are typically in the range of 10 to 100 milliliters per minute, while typical carrier fluid stream 7 flow rates are in the range of 2 to 4 liters per minute.

Pump 21, preferably of the ASF Model No. 5010 or 7010 Oil-less Diaphragm Pump design, circulates fluid stream flow through the system. Filters 22a and 22b, preferably consisting of 100 to 500 cubic centimeters (cc) of activated charcoal combined with 200 to 1000 cc of combined type 5A and 13X molecular sieve, clean the outlet fluid flow stream 6 prior to recirculation back into the IMS sensor 10. A plurality of flow sensors FS, preferably of the Honeywell Model AWM3000 design, are installed to measure flow rates at various points throughout the system. A plurality of flow adjustment valves 50, preferably Model No. SS-2MG4 valves manufactured by Newpro, Inc., are adjusted to initially set the various flow rates in the system to their proper values. These valves 50 are then left at their initial positions during use of the system in making IMS measurements.

Sample fluid stream flow 3 originates from a source of high pressure carrier gas 70 and is injected through an injection solenoid valve 71 into a gas chromatograph preferably comprised of a multicapillary column 72. Carrier gas 70 is preferably injected into the multicapillary column 72 by way of a sample injector 73 prior to entering the sample stream inlet of the IMS sensor 10. Due to the preferred design of the system, the sample fluid stream flow rate 3 through the multicapillary column 72 will be equal to the exhaust fluid stream flow rate 8 and is controlled by means of an adjustable orifice flow restrictor valve 51 located in series with valve 71 and preferably manufactured by the Sibertech Company, Novosibirsk, Russia. Valve 71, which is preferably of the two-way three-port injection solenoid design manufactured by the Sibertech Company either: (i) is positioned to bypass sample injector 73 to allow pure carrier gas 70 to enter the IMS sensor 10 as the sample fluid stream flow 3, or alternately (ii) is positioned to allow the carrier gas 70 to pass through the sample injector 73 to entrain the analyte to be processed by the IMS sensor 10.

Although a multicapillary column design is used as the gas chromatograph in the preferred embodiment, other single capillary and packed column designs in the current state of the art are acceptable for use, so long as a means of flow and temperature control are provided similar to that described herein, and so long as the gas chromatograph is hermetically sealed to the sample stream inlet of the IMS sensor.

The carrier gas 70 is introduced into the flow system at high pressure by means of a conventional pressure regulator and relief valve arrangement. The preferred embodiment utilizes a pressure regulator and relief valve system manufactured by Sibertech Company. Pressure in tank 69 is reduced by the pressure regulator 68 from 100 to 2500 psia at the outlet of tank 69 to 15 to 25 psig at head of the multicapillary column 72. The carrier gas 70 is preferably inert such as pure nitrogen or it can be ultrapure air.

The disadvantage of using nitrogen as the carrier gas 70 is that when the instrument is first turned on some air will already be present in the IMS sensor 10 flow system. As the instrument operates, the pure nitrogen carrier gas will mix with and gradually displace this air. During this period, the composition of the recirculating gas in the IMS sensor 10 flow system will gradually shift from air to nitrogen. However, stable readings cannot be achieved with the IMS sensor 10 until the composition of the recirculating gas for the IMS sensor 10 is stable. Thus operation with nitrogen as the carrier gas 70 would extend the time required for the IMS sensor 10 to reach stable operation. Ultrapure air is the source of carrier gas 70 used in the preferred embodiment.

The sample injector 73 is a hollow container preferably made of metal such as stainless steel and having one wall which is hermetically sealed to the multicapillary column 72. In one configuration, a second wall of the sample injector 73 is comprised of a septum membrane. This membrane is preferably made of silicon or other similar materials such as a Teflon-type elastomer. A gas or liquid sample to be processed by the IMS sensor 10 is preferably injected through the membrane by means of syringe. Since the sample injector 73 is at an elevated temperature (100° C. or greater), liquid samples quickly vaporize once they enter the sample injector 73 volume. In an alternate arrangement, the membrane wall of the sample injector is removed and a sampling cartridge is inserted into the injector. Once in the sample injector 73 the cartridge is rapidly heated, desorbing materials which have been collected on the cartridge's wire mesh collecting surface. In either configuration, the vapor samples present in sample injector 73 are forced onto the multicapillary column 72 by momentarily supplying a pulse of carrier gas 70 to the sample injector 73 volume. The sample fluid stream flow 3 entering the sample stream inlet of the IMS sensor 10 is thus a mixture of carrier gas 70 entrained with unknown concentrations of one or multiple analytes to be analyzed.

Sample fluid stream flow 3 exiting the sample injector 73 is preferably introduced at a rate of 10–100 ml/min and preferably between 50 and 80 ml/min into the multicapillary column 72. The multicapillary column 72 is preferably a hollow bundle of glass capillary tubes that contain a lining known as the stationary phase. These glass tubes range from approximately 25 to 100 micrometers (um) in inner diameter (ID) and are preferably approximately 40 um in ID. The stationary phase can be comprised of substances such as SE-30, SE-54 or carbowax 20M, with SE-54 being used in the preferred embodiment.

DESCRIPTION OF OPERATION

In operation of the system, the carrier gas 70 first passes through the sample injector 73 where samples of the analyte are injected in a pulse-like manner into the carrier gas 70 thereby giving rise to spatially separated carrier gas "slugs" containing various species of the entrained analyte. These entrained analyte carrier gas slugs are then passed through the multicapillary column 72 at the carrier gas 70 flow rate. The molecules comprising the various analyte species present in the sample injector 73 are each soluble to differing extent in the stationary phase substance. Thus all the analyte species entrained in a given carrier gas slug will undergo numerous passages in and out of solution with the stationary phase substance as the carrier gas slug transits the length of the multicapillary column 72. Each analyte species of interest will experience a transit time through the multicapillary column 72 different from the other analyte species present in that carrier gas slug due to the differing extent to which each analyte species is soluble in the stationary phase. This transit time is known as the "retention time" for that particular analyte species. This variation in retention times allows the IMS sensor to achieve improved selectivity in distinguishing between the various analyte species entrained in the carrier gas 70 since the entry of each analyte species into the sample stream inlet of the IMS sensor 10 will be staggered as compared to the other species present in the carrier gas 70. Thus the IMS sensor 10 is required to respond to only a single analyte species at a time thereby preventing a degradation in the IMS measurement by the other species present in the analyte sample.

The multicapillary column 72 is heated by a surrounding oven and maintained within a selected temperature falling within the band of 100°–180° C. to ensure the optimum retention time distribution for the various analyte species of interest. The multicapillary column 72 is hermetically sealed to a transfer line 74 leading to the sample stream inlet of the IMS sensor 10. Transfer fine 74 is preferably maintained at a temperature 10° C. –40° C. above (and most preferably 10° C. above) that of the multicapillary column 72 in order to ensure that analyte species will not adsorb on the walls of the transfer fine 72 instead of entering the sample stream inlet of the IMS sensor 10.

Figure 2:
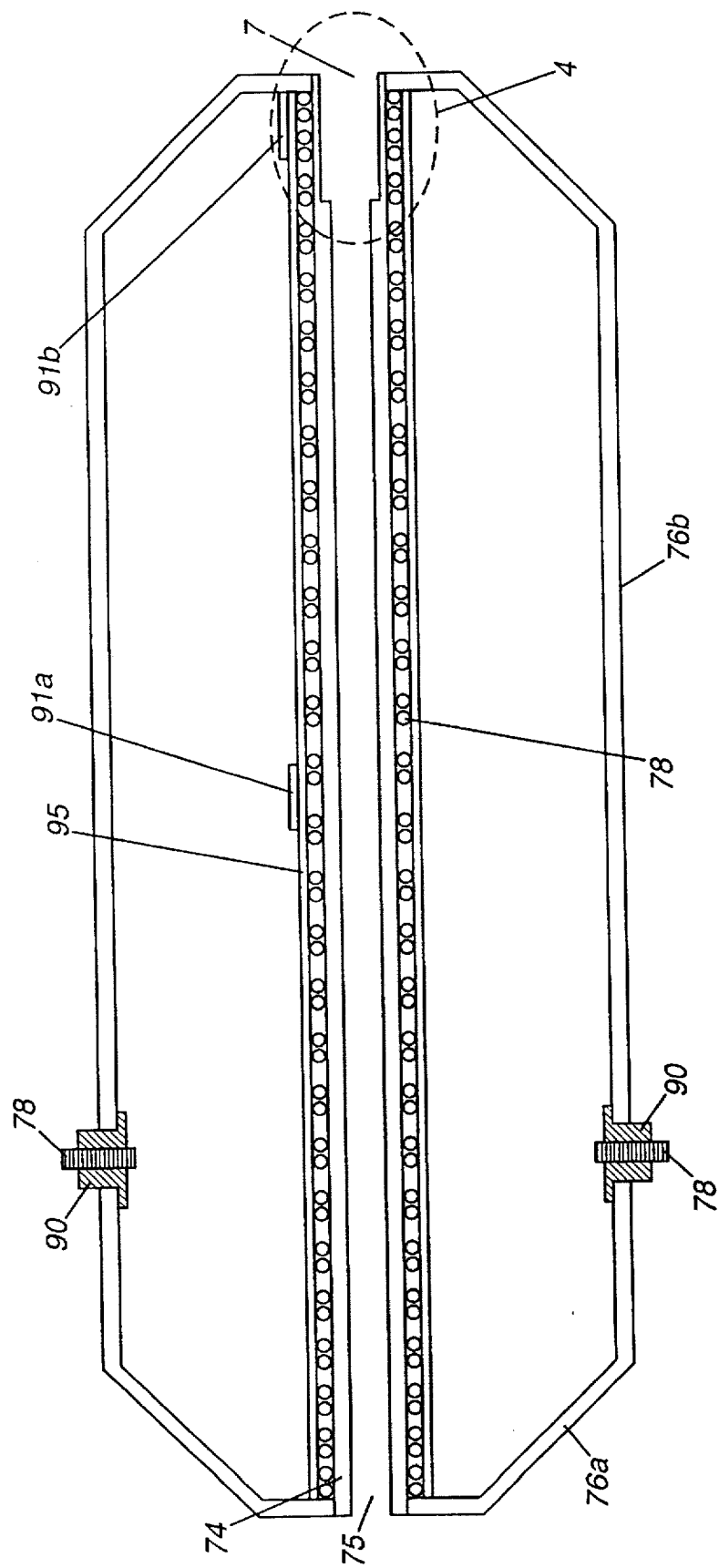
FIG. 2 is a cross-sectional view of a preferred embodiment of the heated transfer line of the present invention.

As shown in FIG. 2, the preferred embodiment of the heated transfer fine 74 is similar to the design disclosed in U.S. patent application Ser. No. 08/627,584 and has a heating element 78 of one or more sections of insulated, high resistance wire, preferably 0.02 inch diameter tetraflouroethylene (TFE)-coated Constantan thermocouple wire, wound around the heated passageway of the transfer line 74 from the inlet end 75 to the outlet end 77 to provide electrical heating to the transfer line passageway 74. Other metals such as platinum that can be formed as a thin fill surrounding the transfer line 74 could be used for the heating element 78. In addition, a flexible heating element 78 in which the thin metal film is embedded in a material such as a clear polyimide film, a fiber paper aramide, or silicon rubber could be used. Additionally, the thin metal fill heating element 78 could be embedded in a rigid mica shell. The heating element wires 78 of the preferred embodiment is wound in a single or preferably a dual-helix fashion around the transfer line passageway 74. Preferably, the heating element wires 78 penetrate through holes in two bonded cylindrical half sections 90 of insulating material such as Kel-F plastic that is embedded between metal shells 76a and 76b. Metal shells 76a and 76b can be welded to transfer line 74 and which are preferably supported by the cylindrical half-sections 90 and O-rings (not shown) or other means known in the art. In the preferred embodiment, a layer of teflon tape 95 preferably holds the heating element wires 78 against the transfer line passageway 74 to improve heat transfer efficiency between the heating element wires 78 and the transfer line passageway 74. To provide a more uniform temperature profile across the length of the passageway 5, the winding density (or pitch) of the heating element wires 78 in the preferred embodiment is increased near the heating device inlet end 75 and outlet end 77 where heat losses are at their maximum.

Two wire resistance thermometers 91a and 91b, each preferably a Minco Thermal-Ribbon platinum resistance-measuring thermometer Model No. S651PDZ24A, are preferably attached to the transfer line passageway 74 to monitor the temperature of the transfer line 74. Other components which could be used for the thermometers 91a and 91b are a thermocouple, a thermistor, and a semiconductor. The first thermometer 91a is preferably positioned near the midpoint of the transfer line 74 while the second thermometer 91b is preferably positioned near the outlet end 77. The thermometers 91a and 91b are preferably connected to a temperature controller which switches power to the heating element section(s) 78 to maintain a substantially uniform temperature profile across the transfer line passageway 74. A conventional resistance-measuring temperature controller preferably compares the temperature measured by the thermometer 91a or 91b to a selected setpoint temperature programmed into the temperature controller. The temperature comparison can be performed by means of an algorithm run on a computer processor by computer software programmed for this purpose that is stored on a computer-readable storage medium. Other means of performing the temperature comparison are also possible, such as use of an electronic integrated differential amplifier circuit, an analog or a combined analog and digital comparison circuit comprised of discrete electrical and digital logic components, or other similar circuitry presently in the state of the art. The temperature control circuitry in the preferred embodiment results in a stabilized temperature profile across the transfer line passageway 74.

Figure 3:
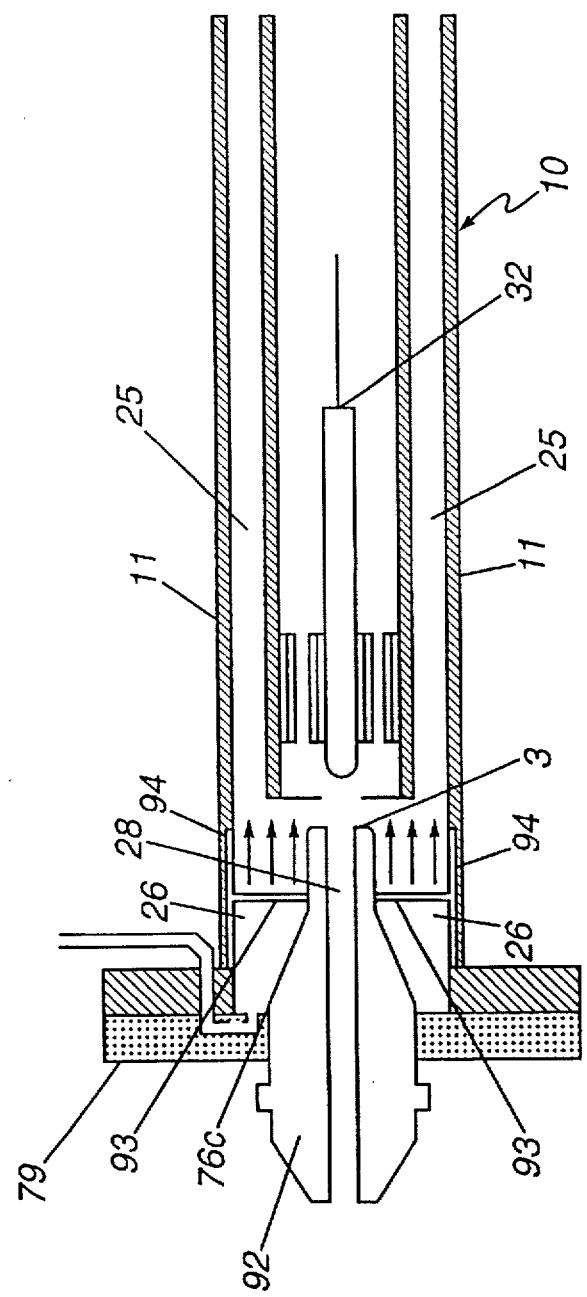
FIG. 3 is a cross-sectional view of an alternate preferred embodiment of a heating device configured with a flow smoothing insert.

As shown in FIG. 3 a flow smoothing insert 93 similar to that shown in U.S. patent application Ser. No. 08/627,584 can be placed in the gap between a heated transfer line shell 76c and the inner surface of the IMS housing 11 to eliminate the turbulence created by the transfer line outlet end 77. The shape of the shell 76c reduces the gap between the IMS housing 11 inner surface and the shell 76c at the transfer line mounting flange 79 while gradually increasing this gap closer to the transfer line outlet end 77. The flow smoothing insert 93 is preferably made of a free pitch stainless steel mesh shaped in the form of a round disc with a center opening concentric with the outer circumference of the disc. Other possible materials for the flow smoothing insert 93 are titanium, stainless steel, gold, nickel and other non-reactive metals having an inherently low vapor pressure characteristic. Other low porosity, low vapor pressure non-reactive, non-metallic materials such as glass, quartz, teflon and sapphire can be used for the flow smoothing insert 93. The flow smoothing insert 93 is preferably slipped over the transfer line outlet end 77 to form an interference fit with the transfer line shell 76c prior to mounting the heating device 1 on the IMS sensor. When the heating device 92 is mounted on the IMS sensor 10 the flow smoothing insert 93 will fill the gap between the transfer line shell 76c and the IMS housing 11 inner surface at a location proximate to the transfer line outlet end 77. Since the surface of the transfer line shell 76c is electrically connected (not shown) to electrode 32 to contribute to the radial electric field created by the bias potential applied to electrode 32, the flow smoothing insert 93 must be electrically insulated from the grounded IMS housing 11. This may be accomplished by placing a band 94 of electrically insulating material such as teflon between the flow smoothing insert 93 and the IMS housing 11 inner surface.

After the inlet heating device 92 is mounted on the IMS sensor 10 with the flow smoothing insert 93 attached, the flow entering the carrier stream plenum 26 of the IMS sensor 10 will undergo gradual volume expansion before being filtered through the flow smoothing insert 93. This gradual volume expansion in combination with the filtering will produce a laminar carrier stream flow profile throughout the volume between the transfer line outlet end 77 and the IMS housing 11 upon exit of the carrier flow stream from the flow smoothing insert 93. This laminar flow profile prevents the sample stream from being mixed with the portion of the carrier stream entering the analytical gap. This in turn will allow increasing the flow entering the carrier stream plenum 26 so that losses in IMS sensitivity due to ion diffusion in the analytical gap are minimized.

While presently preferred embodiments of practicing the invention has been shown and described with particularity in connection with the accompanying drawings, the invention may otherwise be embodied within the scope of the following claims.

What is claimed is:

1. A fluid filtration system for use with an ion mobility spectrometer in gas chromatography applications, comprising:
   A. a pump in communication with both an outlet and a carrier stream inlet of the ion mobility spectrometer for recirculating ion mobility spectrometer outlet fluid flow into the carrier stream inlet;
   B. at least one filter in communication with the pump for removing impurities from the recirculated flow; and
   C. an exhaust for removing a portion of the outlet fluid flow from the system, wherein the amount of fluid removed is equal to the amount of fluid entering a sample stream inlet of the ion mobility spectrometer.

2. The fluid filtration system of claim 1, wherein the ion mobility spectrometer is transportable when connected to the filtration system.

3. The fluid filtration system of claim 1, further comprising:
   A. a first filter in communication with the inlet of the pump;
   B. a second filter in communication with the outlet of the pump; and
   C. a flow restrictor in communication with the sample stream inlet of the ion mobility spectrometer for controlling the amount of fluid entering the sample stream inlet;
   wherein the filters prevent the migration of impurities into the ion mobility spectrometer when the filtration system is not in use.

4. The fluid filtration system of claim 1, further comprising a gas chromatograph column in communication with the flow restrictor and the sample stream inlet of the ion mobility spectrometer.

5. The fluid filtration system of claim 1, further comprising:
   A. a multicapillary gas chromatograph column containing a coating comprised of a stationary phase substance in communication with the sample stream inlet for transmitting an unknown concentration level of at least one analyte into the sample stream inlet to be measured by the ion mobility spectrometer;
   B. a sample injector in communication with the multicapillary column for injecting the at least one analyte into the multicapillary column; and
   C. a source of carrier gas in communication with the sample injector for entraining the at least one analyte for transport into the multicapillary column;
   wherein the at least one analyte is soluble in the stationary phase substance such that transport of the at least one analyte into the sample stream inlet will be delayed by a predetermined time interval in the multicapillary column prior to entering the sample stream inlet to be measured by the ion mobility spectrometer.

6. The fluid filtration system of claim 5, wherein the stationary phase substance is selected from the group consisting of SE-30, SE-54 and carbowax 20M.

7. The fluid filtration system of claim 5, wherein the sample injector contains a septum membrane for injecting the at least one analyte into the carrier gas.

8. The fluid filtration system of claim 5, further comprising a pressure regulator in communication with the source of carrier gas for regulating the pressure of the carrier gas entering the sample injector.

9. The fluid filtration system of claim 5, further comprising a heated transfer line in communication with the multicapillary column and the sample stream inlet for preventing adsorption of the at least one analyte prior to entering the sample stream inlet.

10. The fluid filtration system of claim 1 for use with an ion mobility spectrometer, wherein the ion mobility spectrometer comprises:
    A. a housing having at least one inlet for communication with a sample media and at least one outlet,
    B. an analyzer positioned within the housing comprising:
       (i) at least first and second longitudinally spaced apart electrodes, the space between the electrodes defining a longitudinal analytical gap, the gap being in communication with a source of carrier gas for flow therethrough,
       (ii) an ionization source juxtaposed with the analytical gap and in communication with the inlet for ionization of sample media,
       (iii) an ion aperture defining an opening between the ionization source and the analytical gap,
       (iv) a third electrode positioned proximate to the ion aperture,
       (v) at least one outlet aperture from the analytical gap remote from the ion aperture,
       (vi) an ion detector for measuring ions from the analytical gap and spaced from the electrodes, and
       (vii) an electrical controller connected to the electrodes for impressing:
          (a) direct current potentials to the first, second and third electrodes, and
          (b) a periodic asymmetrical potential to the first and second electrode, the potentials capable of creating a transverse electric field therebetween during the flow of carrier gas in the analytical gap.

11. The fluid filtration system of claim 4 for use with an ion mobility spectrometer, wherein the ion mobility spectrometer comprises:
    A. a housing having at least one inlet for communication with a sample media and at least one outlet,
    B. an analyzer positioned within the housing comprising:
       (i) at least first and second longitudinally spaced apart electrodes, the space between the electrodes defining a longitudinal analytical gap, the gap being in communication with a source of carrier gas for flow therethrough,
       (ii) an ionization source juxtaposed with the analytical gap and in communication with the inlet for ionization of sample media,
       (iii) an ion aperture defining an opening between the ionization source and the analytical gap,
       (iv) a third electrode positioned proximate to the ion aperture,
       (v) at least one outlet aperture from the analytical gap remote from the ion aperture, (vi) an ion detector for measuring ions from the analytical gap and spaced from the electrodes, and (vii) an electrical controller connected to the electrodes for impressing:

(a) direct current potentials to the first, second and third electrodes, and (b) a periodic asymmetrical potential to the first and second electrode, the potentials capable of creating a transverse electric field therebetween during the flow of carrier gas in the analytical gap.

12. The fluid filtration system of claim 5 for use with an ion mobility spectrometer, wherein the ion mobility spectrometer comprises:

A. a housing having at least one inlet for communication with a sample media and at least one outlet, B. an analyzer positioned within the housing comprising:

(i) at least first and second longitudinally spaced apart electrodes, the space between the electrodes defining a longitudinal analytical gap, the gap being in communication with a source of carrier gas for flow therethrough, (ii) an ionization source juxtaposed with the analytical gap and in communication with the inlet for ionization of sample media, (iii) an ion aperture defining an opening between the ionization source and the analytical gap, (iv) a third electrode positioned proximate to the ion aperture, (v) at least one outlet aperture from the analytical gap remote from the ion aperture, (vi) an ion detector for measuring ions from the analytical gap and spaced from the electrodes, and (vii) an electrical controller connected to the electrodes for impressing:

(a) direct current potentials to the first, second and third electrodes, and (b) a periodic asymmetrical potential to the first and second electrode, the potentials capable of creating a transverse electric field therebetween during the flow of carrier gas in the analytical gap.

13. The fluid filtration system of claim 4, further comprising a transfer line in communication with the gas chromatograph column for heating a fluid stream entering the sample stream inlet of an ion mobility spectrometer, the transfer line comprising:

A. a hollow passageway having an inlet end in communication with an outlet end for passage of a sample fluid stream from the gas chromatograph column into the sample stream inlet;

B. a hollow housing attached to both the passageway inlet and outlet ends for mounting the transfer line to the sample stream inlet of the ion mobility spectrometer;

C. an electrical heating element surrounding the surface of the passageway for heating the passageway; and D. a temperature control circuit for controlling electrical power input to the heating element, comprising:

(i) at least one temperature measuring device attached to the surface of the passageway for measuring the temperature of the passageway;

(ii) a temperature controller having an input electrically connected to the temperature measuring device and an output electrically connected to the heating element for:

(a) comparing the temperature measured by the temperature measuring device to a predetermined reference value; and (b) adjusting the electrical power input to the heating element to substantially match the temperature of the passageway to the reference value.

14. The transfer line of claim 13, wherein the housing is attached to the passageway to form a hermetic seal between the housing and the passageway.

15. The transfer line of claim 13, wherein the space between the passageway and the housing is filled with a heat insulating material.

16. The transfer line of claim 13, wherein the housing is attached to a flange mounted to the sample stream inlet to form a gas-tight attachment between the device and the sample stream inlet.

17. The transfer line of claim 13, wherein the heating element comprises a high resistance metal wire wound around the passageway from the inlet end to the outlet end.

18. The transfer line of claim 17, wherein the density of the winding is increased at both ends of the heating element.

19. The transfer line of claim 13 wherein the temperature measuring device is selected from the group consisting of an electrical resistance measuring thermometer, a thermocouple, a thermistor and a semiconductor.

20. The transfer line of claim 13, wherein the temperature controller is a device selected from the group consisting of a computer processor, an electronic integrated differential amplifier circuit, an analog comparison circuit comprised of discrete electrical components and a combined analog and digital comparison circuit comprised of discrete electrical and digital logic components.

21. The transfer line of claim 13, further comprising an element for reducing turbulence in a flow stream entering the carrier stream inlet of the ion mobility spectrometer, comprising an insert of porous material placed between the transfer line housing and the surface of the sample stream inlet at a location proximate to the outlet end of the transfer line, wherein the insert fills the gap between the transfer line housing and the sample stream inlet surface.

22. The transfer line of claim 21, wherein the insert is comprised of a non-metallic material.

23. The transfer line of claim 22, wherein the non-metallic material is selected from the group consisting of glass, quartz, teflon and sapphire.

24. The transfer line of claim 21, wherein the porous material comprises a meshed metal selected from the group consisting of stainless steel, titanium, nickel, gold and other non-reactive metals having an inherently low vapor pressure characteristic, and further comprising a band of electrically insulating material placed between the insert and the sample stream inlet surface for electrically isolating the sample stream inlet surface from the insert.

25. The transfer line of claim 21, wherein the insert is shaped as a round disc with a center opening concentric with the insert outer circumference for attaching the insert to the transfer line such that the insert surrounds the transfer line housing.

26. The transfer line of claim 21, wherein the transfer line housing is electrically connected to the ion mobility spectrometer for establishing an electric field at the sample stream inlet of the ion mobility spectrometer.

27. The transfer line of claim 24, wherein the insert is electrically isolated from the ion mobility spectrometer.

\* \* \* \* \*

UNITED STATES PATENT AND TRADEMARK OFFICE
CERTIFICATE OF CORRECTION

PATENT NO. : 5,736,739
DATED : April 7, 1998
INVENTOR(S) : Robert E. Uber, Viktor Kousnetsov, Alexander Tarassov, Byron L. Carnahan, Charles W. Pipich It is certified that error appears in the above-indentified patent and that said Letters Patent is hereby corrected as shown below:

Column 7, line 46: change "the" to "a"
Column 10, line 7: change "transfer line" to "fluid filtration system"
Column 10, line 10: change "tranfer line" to "fluid filtration system"
Column 10, line 13: change "transfer line" to "fluid filtration system"
Column 10, line 17: change "transfer line" to "fluid filtration system"
Column 10, line 20: change "transfer line" to "fluid filtration system"
Column 10, line 22: change "transfer line" to "fluid filtration system"
Column 10, line 26: change "transfer line" to "fluid filtration system"
Column 10, line 33: change "transfer fine" to "fluid filtration system"
Column 10, line 37: change "fine" to "line"
Column 10, line 41: change "transfer fine" to "fluid filtration system"
Column 10, line 43: change "transfer line" to "fluid filtration system"
Column 10, line 46: change "transfer fine" to "fluid filtration system"
Column 10, line 54: change "transfer line" to "fluid filtration system"
Column 10, line 59: change "transfer line" to "fluid filtration system"
Column 10, line 63: change "transfer line" to "fluid filtration system"
Column 10, line 15, change "device" to "transfer line"

Column 5, line 24: change "fine" to "line"
Column 5, line 31: change "fine" to "line"
Column 5, line 60: change "5" to "74"

Figure 2: change "7" to "77"

Signed and Sealed this

Fourteenth Day of July, 1998

Attest:

BRUCE LEHMAN

Attesting Officer

Commissioner of Patents and Trademarks